(12) United States Patent
Ebert et al.

(10) Patent No.: US 6,590,058 B1
(45) Date of Patent: Jul. 8, 2003

(54) OLIGOMERIC BISCHLOROCARBONIC ACID ESTERS OBTAINED FROM SELECTED CYCLOALIPHATIC BISPHENOLS AND OTHER BISPHENOLS

(75) Inventors: Wolfgang Ebert, Krefeld (DE); Burkhard Köhler, Leverkusen (DE); Yun Chen, Shanghai (CN)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/049,774

(22) PCT Filed: Jul. 6, 2000

(86) PCT No.: PCT/EP00/06380

§ 371 (c)(1),
(2), (4) Date: Mar. 20, 2002

(87) PCT Pub. No.: WO01/05869

PCT Pub. Date: Jan. 25, 2001

(30) Foreign Application Priority Data

Jul. 19, 1999 (DE) .......................................... 199 33 070
Dec. 22, 1999 (DE) .......................................... 199 62 016

(51) Int. Cl.[7] .............................................. C08G 64/00
(52) U.S. Cl. ........................................ 528/196; 528/198
(58) Field of Search ................................. 528/196, 198

(56) References Cited

U.S. PATENT DOCUMENTS

| | | | |
|---|---|---|---|
| 4,920,200 A | 4/1990 | Brunelle et al. | 528/370 |
| 4,982,014 A | 1/1991 | Freitag et al. | 568/721 |
| 5,126,428 A | 6/1992 | Freitag et al. | 528/196 |
| 5,227,458 A | 7/1993 | Freitag et al. | 528/196 |
| 6,156,871 A | 12/2000 | Köhler et al. | 528/371 |
| 6,297,346 B1 | 10/2001 | Köhler et al. | 528/196 |

FOREIGN PATENT DOCUMENTS

| | | |
|---|---|---|
| DE | 1 301 908 | 8/1969 |
| EP | 0 362 792 | 4/1990 |
| EP | 0 414 083 | 2/1991 |
| EP | 0 691 361 | 1/1996 |
| EP | 0 827 948 | 3/1998 |

*Primary Examiner*—Terressa M. Boykin
(74) *Attorney, Agent, or Firm*—Joseph C. Gil; Aron Preis

(57) ABSTRACT

This invention relates to oligomeric bischloroformic acid esters which are obtainable, in a two-phase reaction, from selected cycloaliphatic bisphenols and other bisphenols by introducing phosgene.

13 Claims, No Drawings

OLIGOMERIC BISCHLOROCARBONIC ACID ESTERS OBTAINED FROM SELECTED CYCLOALIPHATIC BISPHENOLS AND OTHER BISPHENOLS

This invention relates to oligomeric bischloroformic acid esters which are obtainable, in a two-phase reaction, from selected cycloaliphatic bisphenols and other bisphenols by introducing phosgene.

Bischloroformic acid esters are suitable as educts for the production of cyclic polycarbonate compounds (as a precursor for high-molecular polycarbonates in accordance with DE 19 636 539) and of linear polycarbonates, for example, from solution polymerisation.

The bisphenol 1,1-bis(hydroxyphenyl)-3,3,5-trimethylcyclohexane (TMC bisphenol) produces polycarbonates having a high glass temperature. Polycarbonates having a lower glass temperature are often required, because of their better workability.

Suitable compounds are, for example, copolymers with other bisphenols.

It is in principle possible to mix an oligomeric bischloroformic acid ester precursor of TMC bisphenol (precursor 1; V1) with another oligomeric bischloroformic acid ester precursor (precursor 2; V2) prior to the reaction. But a statistical sequence of the monomeric bisphenols (V1) and (V2) is not then obtained during the subsequent reaction, and blocks of precursor 1 and precursor 2 are formed instead. For this reason it is desirable to prepare oligomeric bischloroformic acid ester precursors which are themselves built up statistically from TMC bisphenol and other bisphenols.

The invention accordingly provides mixtures of bischloroformic acid esters corresponding to formulae (I), (II) and (III)

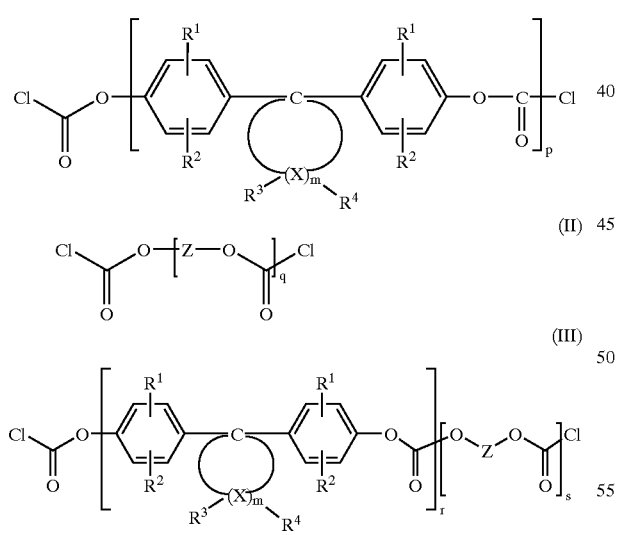

wherein
R$^1$ and R$^2$ independently of one another denote hydrogen, halogen, preferably chlorine or bromine, C$_1$–C$_8$-alkyl, C$_5$–C$_6$-cycloalkyl, C$_6$–C$_{10}$-aryl, preferably phenyl, and C$_7$–C$_{12}$-aralkyl, preferably phenyl-C$_1$–C$_4$-alkyl, in particular benzyl, m is an integer from 4 to 7, preferably 4 or 5, R$^3$ and R$^4$ independently of one another denote hydrogen or C$_1$–C$_6$-alkyl and X denotes carbon, with the proviso that, on at least one X atom per repeat unit in (I) or (III), R$^3$ and R$^4$ simultaneously denote alkly, Z is an aromatic group having 6 to 30 C atoms and can contain one or more aromatic nuclei, can be substituted and can contain aliphatic groups or cycloaliphatic groups which differ from the cycloaliphatic groups in (I), or hetero atoms as bridge-type cross-links, p, q, r and s represent a natural number from 1 to 15 and the molar ratio of the cycloaliphatic bisphenol units to the aliphatic bisphenol units is 1:10 to 10:1.

Z is preferably

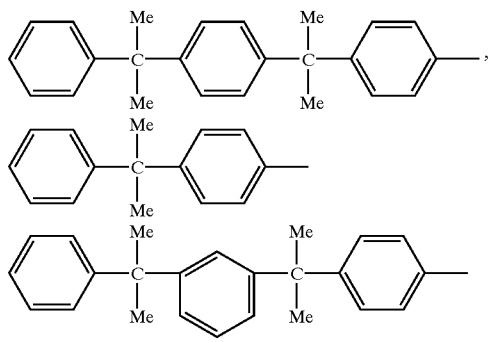

wherein Me=methyl group.

The mixtures of bischloroformic acid esters are preferably prepared by introducing phosgene into a mixture of bisphenols corresponding to formulae (IV) and (V) in the molar ratio of 1:10 to 10:1

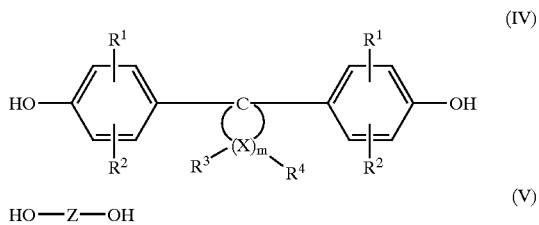

in a two-phase system consisting of water and an organic solvent, preferably methylene chloride, at −5° C. to 40° C., the pH value of the aqueous phase being maintained at between 1 and 13, preferably between 2 and 9, by the addition or previous provision of an alkali metal hydroxide or alkaline-earth hydroxide.

Here X, R$^1$, R$^2$, R$^3$, R$^4$ and m have the meanings given for formula (I).

Preferably on 1 to 2 X atoms and in particular on only one X atom per molecule (IV), R$^3$ and R$^4$ simultaneously denote alkyl.

The preferred alkyl group is methyl. The X atoms in the a-position to the diphenyl-substituted C atom (C-1) are preferably not dialkyl-substituted, but alkyl disubstitution is preferred in the β-position to C-1.

Dihydroxydiphenylcycloalkanes having 5 and 6 C atoms in the ring in the cycloaliphatic group (m=4 or 5 in formula (IV)) are preferred, for example, the diphenols corresponding to formulae (IVa) to (IVc)

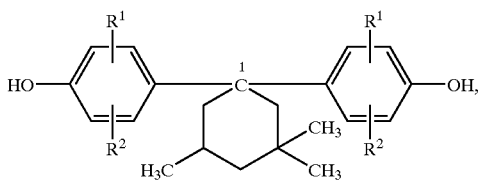

(IVa)

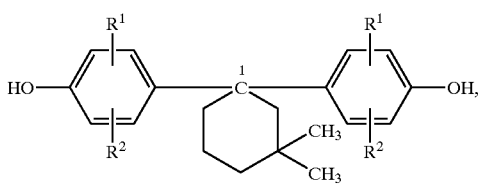

(IVb)

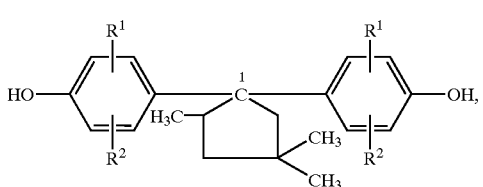

(IVc)

wherein 1,1-bis(4-hydroxyphenyl)-3,3,5-trimethylcyclohexane (formula (IVa) with $R^1$ and $R^2$ denoting H) is particularly preferred. The polycarbonates can be produced from diphenols corresponding to formula (I), in accordance with the German Patent Application P 3 832 396.6.

For the repeat units, other diphenols, for example, corresponding to formula (V)

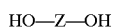 (V)

are used in addition to the diphenols corresponding to formula (IV). Suitable diphenols corresponding to formula (V) are those wherein Z is an aromatic group having 6 to 30 C atoms and can contain one or more aromatic nuclei, can be substituted and can contain aliphatic groups or cycloaliphatic groups other than those corresponding to formula (I) or hetero atoms as bridge-type cross-links.

Examples of diphenols corresponding to formula (V) are: hydroquinone, resorcinol, dihydroxydiphenyls, bis(hydroxyphenyl)alkanes, bis(hydroxyphenyl)cycloalkanes, bis(hydroxyphenyl) sulfides, bis(hydroxyphenyl) ethers, bis(hydroxyphenyl) ketones, bis(hydroxyphenyl) sulfones, bis(hydroxyphenyl) sulfoxides, α,α'-bis(hydroxyphenyl)diisopropylbenzenes as well as ring-alkylated and ring-halogenated compounds thereof.

Preferred diphenols are α,α'-bis(hydroxyphenyl)-m-diisopropylbenzene, α,α'-bis(hydroxyphenyl)-p-diisopropylbenzene and 2,2-bis(4-hydroxyphenyl)propane; α,α'-bis(hydroxyphenyl)-m-diisopropylbenzene and 2,2-bis(4-hydroxyphenyl)propane are particularly preferred.

These and other suitable diphenols are described, for example, in the monograph: H.Schllell. "Chemistry and Physics of Polycarbonates", Interscience Publishers, New York. 1964.

Mixtures of bisphenols (V) and of other bisphenols may, of course, also be used as cobisphenols.

For this, examples of other preferred bisphenols are: 4,4'-dihydroxydiphenyl, 2,4-bis(4-hydroxyphenyl)-2-methylbutane, 1,1-bis(4-hydroxyphenyl)cyclohexane, α,α'-bis(hydroxyphenyl)-p-diisopropylbenzene, 2,2-bis(3-methyl-4-hydroxyphenyl)propane, 2,2-bis(3-chloro-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4,4-hydroxyphenyl) sulfone, 2,4-bis(3,4-dimethyl-4-hydroxyphenyl)-2-methylbutane, 1,1-bis(3,5-dimethyl-4-hydroxyphenyl)cyclohexane, 2,2-bis(3,5-dichloro-4-hydroxyphenyl)propane and 2,2-bis(3,5-dibromo-4-hydroxyphenyl)propane.

Compounds used as bisphenols corresponding to formula (IV) are preferably 1,1-bis(hydroxyphenyl)-3,3,5-trimethylcyclohexane or 1,1 -bis(hydroxyphenyl)-3-methylcyclohexane, particularly preferably 1,1-bis(hydroxyphenyl)-3,3,5-trimethyl-cyclohexane.

Compounds used as bisphenols corresponding to formula (V) are preferably 2,2-bis(hydroxyphenyl)propane (BPA), 1,1-bis(hydroxyphenyl)ethane or 2,2-bis(hydroxyphenyl)butane, particularly preferably 2,2-bis(hydroxyphenyl)propane.

The invention also provides the use of the mixtures of bischloroformic acid esters according to the invention for the production of cyclic cooligocarbonates.

The synthesis of the cyclic cooligocarbonates is carried out by synchronous addition of the solution of the mixtures of bischloroformic acid esters in methylene chloride and of 3 to 15 mol. % of an organic amine, preferably triethylamine, to a two-phase mixture of methylene chloride and water, during which the pH value of the aqueous phase is maintained at between 7 and 13, preferably between 9 and 11,by the addition or previous provision of an alkali metal hydroxide or alkaline-earth hydroxide, and the temperature is 0° C. to 40° C., preferably 30° C. to 40° C. If necessary, in addition up to 10 mol. % of other bisphenols are added.

The invention also provides the use of the mixtures of bischloroformic acid esters according to the invention for the production of linear statistical copolycarbonates.

The high-molecular polycarbonates obtained from the bischloroformic acid esters according to the invention, optionally in combination with other bischloroformic acid esters, can be produced by the known processes for polycarbonate production, preferably by the phase interface process (cf. H. Schnell, "Chemistry and Physics of Polycarbonates", Polymer Reviews, Vol. IX, page 33 ff., Interscience Publishers, 1964.)

The synthesis of the linear statistical copolycarbonates is carried out, for example, by a two-phase reaction of a solution of the mixtures of bischloroformic acid esters in methylene chloride with inorganic bases, preferably alkali metal hydroxides, dissolved in water, at a pH value of 7 to 13 and at a temperature of 0° C. to 40° C. in the presence of 0.01 to 2 mol. % of an organic amine, preferably triethylamine or N-ethylpiperidine, with 0 to 80 mol. % bisphenols corresponding to formulae (IV) and (V) and 0 to 7 mol. % monophenols possibly being added.

Monofunctional compounds in conventional concentrations are used as chain stoppers for the known per se control of the molecular weight of the polycarbonates. Suitable compounds are, for example, phenol, tert. butylphenols or other alkyl-substituted phenols. In particular, small quantities of phenols corresponding to formula (VI)

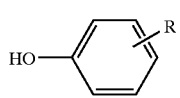 (VI)

wherein

R denotes a branched $C_8$- and/or $C_9$-alkyl group are suitable for controlling the molecular weight.

In the alkyl group R the proportion of CH₃ protons is preferably between 47% and 89% and the proportion of CH— and CH₂, protons is preferably between 53% and 11%; equally preferably, R is in the o- and/or p-position to the OH group, and particularly preferably the upper limit of the ortho proportion is 20%. The chain stoppers are generally used in quantities of from 0.5 to 10 mol. %, preferably 1.5 to 8 mol. %, based on diphenols used.

The copolycarbonates obtained have neither block-type nor alternating structures. They are built up statistically.

The invention is explained in more detail by the following Examples.

EXAMPLES

Example 1

Preparation of a Bischloroformic Acid Ester Mixture According to the Invention 300 g phosgene was introduced, at 0° C. and over a period of 150 minutes, into a mixture consisting of 155 g (0.5 mol) TMC bisphenol, 114 g (0.5 mol) BPA and 1.21 methyl chloride. At the same time, 25 per cent NaOH was added so that the pH value of the mixture was between 2 and 5. Approximately 1 liter NaOH was required for this. After the introduction of the phosgene, the pH value was adjusted to 8 to 9 and nitrogen was passed in until the solution was free from phosgene. After the phase separation, the organic phase was washed with 1N HCl and then with water, dried over sodium sulfate and evaporated. The yield was 285 g, the content of hydrolysable chlorine was 14.5%. A mixture of unoligomerised bischlorofornic acid esters would contain theoretically 18.0% hydrolysable chlorine. A proportion of oligochloroformic acid esters having p, q, r and s of >1 is therefore present.

Example 2

Preparation of a Cyclic Oligocarbonate
(Example of Use)

200 ml methylene chloride, 7 ml water, 2 ml 9.75 molar NaOH in water and 2.4 ml triethylamine were placed in a 1 liter flask and at 40° C., synchronously and with vigorous stirring, 200 ml of a solution in methylene chloride of 78.8 g of the bischloroformic acid ester mixture from Example 1, 59 ml of a 0.75 molar NaOH solution in water and 25 ml of a 10% solution of triethylamine in methylene chloride were introduced over a period of 28 minutes, the introduction of the solution of bischloroformic acid esters being carried out below the surface of the liquid. After the phase separation, the product was washed with 1N HCl and three times with water and the organic phase was evaporated. 60.2 g of a material, which according to HPLC consisted to the extent of approximately 80% of cyclic compounds, was obtained.

Example 3

Preparation of a Linear Polycarbonate
(Example of Use)

39.4 g of the bischloroformic acid esters from Example 1, 62 g 45% NaOH, 0.53 g p-tert. butylphenol and 400 g methylene chloride were placed in a flask, 0.1 g N-ethylpiperidine was added thereto and the mixture was then stirred for 1 hour. The mixture was acidified with HCl, the organic phase was separated off and evaporated in a vacuum drying oven. 30 g of a polycarbonate having a relative solution viscosity of 1.29 (0.5% in methylene chloride at 25° C.) and a glass temperature of 199° C. was obtained.

What is claimed is:

1. A mixture of bischloroformic acid esters corresponding to formulae (I), (II) and (III)

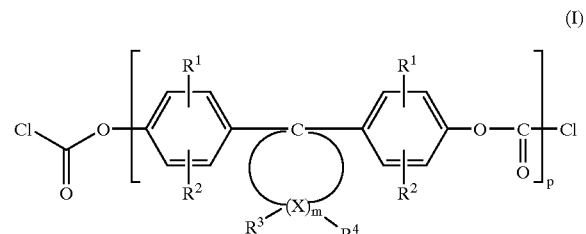

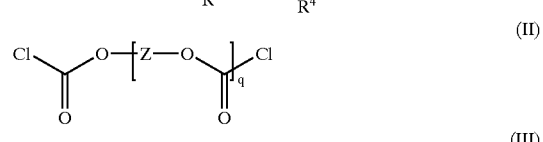

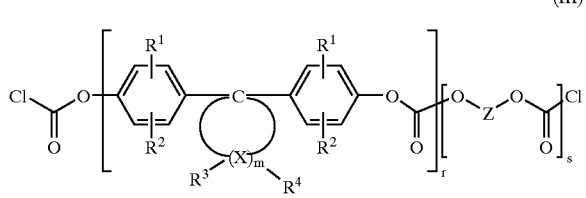

wherein

R¹ and R² independently of one another denote hydrogen, halogen, C₁₋₈-alkyl, C₅₋₆-cycloalkyl, C₆₋₁₀-aryl, and C₇₋₁₂-aralkyl, m is an integer of 4 to 7, R³ and R⁴ independently of one another denote hydrogen or C₁₋₆-alkyl, and X denotes carbon, with the proviso that on at least one X atom per repeat unit, R³ and R⁴ simultaneously denote alkyl, Z is an aromatic group having 6 to 30 carbon atoms, p, q, r and s denote natural numbers of 1 to 15 and the molar ratio of cycloaliphatic bisphenol units to the aliphatic bisphenol units is 1:10 to 10:1.

2. The mixture of claim 1 wherein R¹ and R² independently of one another denote chlorine or bromine.

3. The mixture of claim 1 wherein R¹ and/or R² independently of one another denote phenyl.

4. The mixture of claim 1 wherein R¹ and/or R² independently of one another denote phenyl-C₁₋₄-alkyl.

5. The mixture of claim wherein R¹ and/or R² independently of one another denote benzyl.

6. The mixture of claim 1 wherein m is 4 or 5.

7. The mixture of claim 1 wherein Z further contains one or more aromatic nuclei.

8. The mixture of claim 1 wherein Z is substituted.

9. The mixture of claim 1 wherein Z further contains at least one member selected from the group consisting of aliphatic moieties and cycloaliphatic moieties excluding the cycloaliphatic moieties in (I).

10. The mixture of claim 1 wherein Z further contains hetero atoms.

11. A process of using the mixture of claim 1 comprising producing a cyclic cooligocarbonate.

12. A process of using the mixture of claim 1 comprising producing a linear statistical copolycarbonate.

13. The mixture of claim 1 wherein Z is a member selected from the group consisting of

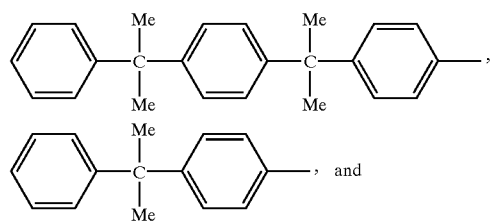
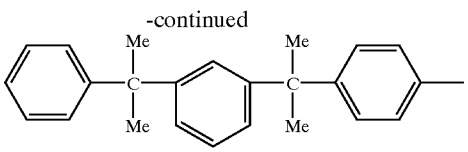
wherein Me denotes a methyl group.
* * * * *